(12) United States Patent
Kitamura et al.

(10) Patent No.: US 9,029,613 B2
(45) Date of Patent: May 12, 2015

(54) ALICYCLIC ALCOHOL

(75) Inventors: Mitsuharu Kitamura, Kurashiki (JP);
Yoshiharu Ataka, Wakayama (JP);
Kazuyuki Fukuda, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/977,221

(22) PCT Filed: Dec. 27, 2011

(86) PCT No.: PCT/JP2011/080149
§ 371 (c)(1),
(2), (4) Date: Sep. 10, 2013

(87) PCT Pub. No.: WO2012/090977
PCT Pub. Date: Jul. 5, 2012

(65) Prior Publication Data
US 2013/0345477 A1 Dec. 26, 2013

(30) Foreign Application Priority Data
Dec. 28, 2010 (JP) ................. 2010-292939

(51) Int. Cl.
| | | |
|---|---|---|
| C07C 31/135 | (2006.01) | |
| C11B 9/00 | (2006.01) | |
| C07C 29/147 | (2006.01) | |
| C07C 29/149 | (2006.01) | |
| C07C 53/44 | (2006.01) | |

(52) U.S. Cl.
CPC ............. *C07C 31/1355* (2013.01); *C07C 53/44* (2013.01); *C07C 29/149* (2013.01); *C07C 31/135* (2013.01); *C07C 2101/14* (2013.01); *C11B 9/0034* (2013.01); *C07C 29/147* (2013.01)

(58) Field of Classification Search
USPC .......................................... 568/826, 825, 822
See application file for complete search history.

(56) References Cited

U.S. PATENT DOCUMENTS

| 3,993,604 | A | 11/1976 | Thomas et al. |
| 5,104,851 | A | 4/1992 | Fujikura et al. |
| 2009/0163733 | A1 | 6/2009 | Joulain et al. |

FOREIGN PATENT DOCUMENTS

| EP | 0328116 | 8/1989 |
| JP | 50 35351 | 4/1975 |
| JP | 1 207251 | 8/1989 |
| JP | 1 207252 | 8/1989 |
| JP | 7 118119 | 5/1995 |
| JP | 9 328451 | 12/1997 |
| JP | 11 300492 | 11/1999 |
| JP | 2000 34243 | 2/2000 |
| JP | 2001 31608 | 2/2001 |
| JP | 2001 199806 | 7/2001 |
| JP | 2001 328909 | 11/2001 |
| JP | 2005 75730 | 3/2005 |
| JP | 2007 537211 | 12/2007 |
| JP | 2009 149577 | 7/2009 |

OTHER PUBLICATIONS

Kinney, C. R. et al. J. org. Chem. 1941, 6, 612-625.*
Bhatia, S. P. et al. Food and Chemical Toxicology 2008, 46, S128-S130.*
JP200034243 (machine translated English Abstract).*
JP200131608 (machine translated English Abstract).*
JP2009149577 (machine translated English Abstract).*
JP2001199806 (machine translated English Abstract).*
JP2001328909 (machine translated English Abstract).*
JP200575730 (machine translated English Abstract).*
JPH07118119 (machine translated English Abstract).*
JPH01207252 (machine translated English Abstract).*
JPH09328451 (machine translated English Abstract).*
JPH11300492 (machine translated English Abstract).*
International Search Report Issued Feb. 14, 2012 in PCT/JP11/80149 Filed Dec. 27, 2011.
U.S. Appl. No. 13/977,274, filed Sep. 4, 2013, Kitamura, et al.
Office Action issued Jul. 28, 2014, in Chinese Patent Application No. 201180068681 (with English Translation).

* cited by examiner

*Primary Examiner* — Clinton Brooks
*Assistant Examiner* — Medhanit Bahta
(74) *Attorney, Agent, or Firm* — Oblon, McClelland, Maier & Neustadt, L.L.P.

(57) ABSTRACT

Provided is an alicyclic alcohol compound which can be used as a raw material for a compound perfume, and which has excellent floral-green-like aromas which are crisp and fresh; also provided are a manufacturing method for the same, and a perfume composition which contains the alicyclic alcohol compound. An alicyclic alcohol compound having a specified structure represented by chemical formula (1) has excellent floral-green-like aromas which are crisp and fresh; and a method for manufacturing the alicyclic alcohol compound represented by chemical formula (1) by reacting, in the presence of hydrogen fluoride, 4-isopropyl-1-methylcyclohexene and carbon monoxide, isomerizing the resulting 4-isopropyl-1-methylcyclohexane carboxylic acid fluoride, thus making 2-methyl-2-(4-methylcyclohexyl)-propionyl fluoride, reacting with alcohol and acquiring a cyclohexane carbonyl compound, and then reducing the cyclohexane carbonyl compound.

3 Claims, No Drawings

ALICYCLIC ALCOHOL

TECHNICAL FIELD

The present invention relates to an alicyclic alcohol compound which can be used as a raw material for compounded perfumes, a method for manufacturing the same, and a perfume composition containing said alicyclic alcohol compound.

BACKGROUND ART

It is known that some of alicyclic alcohol compounds are useful for a raw material for compounded perfumes. For example, Non-patent Document 1 discloses that Mayol having green and muguet-like fragrance, Mugetanol having muguet-like light floral fragrance, Patchone having patchouli-like woody fragrance and the like are useful as a raw material for compounded perfumes.

PRIOR ART DOCUMENTS

Non-Patent Document

Non-Patent Document 1: "Fundamentals of perfume and fragrance preparation", edited by Mototaka Nakajima, 1995, pages 141-144, Sangyo-Tosho Publishing Co., Ltd.

DISCLOSURE OF THE INVENTION

Problems to be Solved by the Invention

The object of the present invention is to provide a novel alicyclic alcohol compound having floral-green-like fragrance useful for a raw material for compounded perfumes, a method for manufacturing the same and a perfume composition containing said alicyclic alcohol compound.

Means for Solving the Problems

As a result of synthesizing various compounds and studying fragrances thereof, the present inventors have found that the alicyclic alcohol compound represented by the following chemical formula (1) which is a novel compound has excellent floral-green-like fragrance with a crisp and fresh feeling.

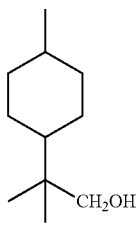

(1)

That is, the present invention relates to a novel alicyclic alcohol compound, a method for manufacturing the same and a perfume composition containing said alicyclic alcohol compound, as follows:
[1] An alicyclic alcohol compound represented by chemical formula (1).
[2] A perfume composition containing an alicyclic alcohol compound represented by chemical formula (1).
[3] A method for manufacturing an alicyclic alcohol compound represented by chemical formula (1) by reacting, in the presence of hydrogen fluoride, 4-isopropyl-1-methylcyclohexene represented by chemical formula (2) with carbon monoxide, isomerizing the resulting 4-isopropyl-1-methylcyclohexane carboxylic acid fluoride represented by chemical formula (3) to obtain 2-methyl-2-(4-methylcyclohexyl)propionyl fluoride, represented by chemical formula (4), reacting said 2-methyl-2-(4-methylcyclohexyl)propionyl fluoride with alcohol to obtain a cyclohexane carbonyl compound represented by general formula (5), and reducing the cyclohexane carbonyl compound represented by general formula (5) to obtain said alicyclic alcohol compound represented by chemical formula (1),

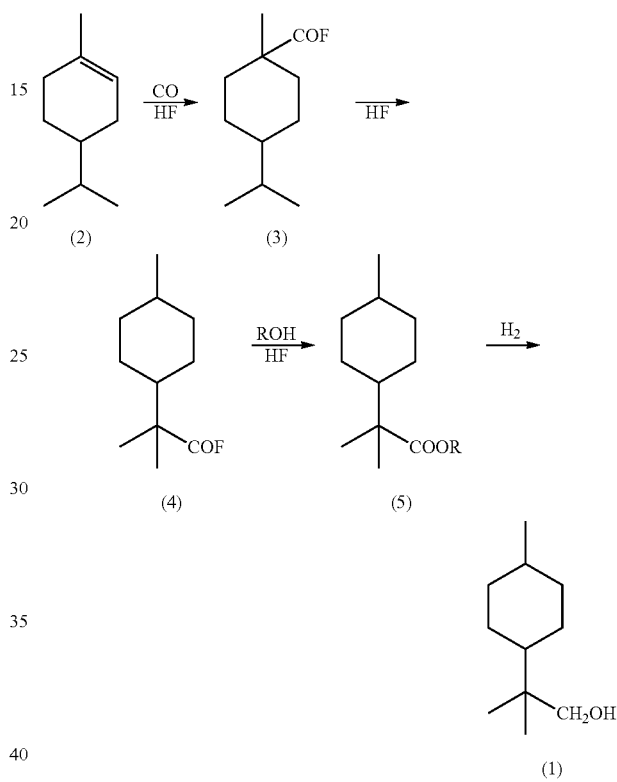

wherein "R" represents an alkyl group having 1-4 carton acorns.

Effect of the Invention

The novel alicyclic alcohol compound of the present invention is novel in terms of having excellent floral-green-like fragrance with a crisp and fresh feeling. Because of its excellent fragrance sustaining properties, it is useful as a perfuming ingredient for a wide variety of products such as toiletry products, soaps and detergent for clothing.

In addition, the manufacturing method for producing the alicyclic alcohol compound of the present invention enables to produce said alicyclic alcohol compound by an industrially beneficial process.

MODES FOR CARRYING OUT THE INVENTION

Novel Alicyclic Alcohol Represented by Chemical Formula (1):

The novel alicyclic alcohol compound of the present invention is represented by chemical formula (1). According to the structure represented by chemical formula (1), a cis isomer and a trans isomer can be existed depending on the substitution formation of 1-position and 4-position of the cyclohexane ring. As for the structure of the novel alicyclic alcohol compound of the present invention, a cis isomer or a trans isomer can be used independently, or a mixture thereof can be used.

The novel alicyclic alcohol compound represented by the above chemical formula (1) has excellent floral-green-like fragrance with a crisp and fresh feeling, and can be used, independently or in combination with other components, as a perfuming ingredient for soap, shampoo, rinse, detergent, cosmetics, spray products, aromatic substances, perfumes, bath additives and the like.

Perfume Composition:

The perfume composition of the present invention can be obtained by combining the novel alicyclic alcohol compound represented by chemical formula (1) with other perfume components conventionally used and/or compounded perfumes having desired composition. The combination ratio depends on the types of compounded perfumes, the types and strength of intended fragrance, or the like. It is preferable to combine the novel alicyclic alcohol compound in an amount of 0.01 to 90% by mass, more preferably in an amount of 0.1 to 50% by mass.

Examples of fragrance materials which can be combined with the novel alicyclic alcohol compound of the present invention include natural essential oils, natural extracts and synthetic perfumes of hydrocarbons, alcohols, phenols, esters, carbonates, aldehydes, ketones, acetals, ethers, nitryls, carboxylic acids, lactones or the like.

Method for Manufacturing Novel Alicyclic Alcohol:

The method for manufacturing the novel alicyclic alcohol compound of the present invention comprises
(a) a process of reacting a monoene compound represented by chemical formula (2) with carbon monoxide in the presence of hydrogen fluoride (hereinafter, "HF") to obtain acid fluoride represented by chemical formula (3) (hereinafter, "carbonylation process"),
(b) a process of isomerizing said acid fluoride represented by chemical formula (3) to acid fluoride represented by chemical formula (4) (hereinafter, "isomerization process"),
(c) a process of reacting the resulting acid fluoride represented by chemical formula (4) with alcohol to obtain a cyclohexane carbonyl compound represented by general formula (5) (hereinafter, "esterification process"), and
(d) a process of reducing the resulting cyclohexane carbonyl compound to obtain the alicyclic alcohol compound represented by chemical formula (1) (hereinafter, "carbonyl group-reduction process").

<(a) Carbonylation Process>

The carbonylation reaction of the monoene compound is carried out in the presence of HF under pressure of carbon monoxide. Thereby, the alicyclic carbonyl compound represented by chemical formula (3) is obtained together with various by-products including other isomers.

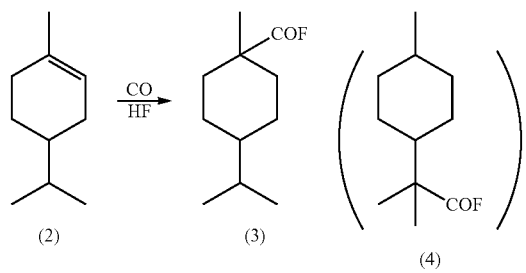

[Monoene Compound]

The monoene compound represented by chemical formula (2) can be synthesized by partial hydrogenation of a corresponding diene compound in the presence of a hydrogenation catalyst.

The monoene compound thus synthesized can be used after removing catalyst by filtration or the like and/or purifying by distillation or the like. Usually, the monoene compound thus synthesized is subjected to carbonylation reaction directly only after removing catalyst without removing solvents used in the reaction process of the monoene compound or removing reaction by-products which are fully hydrogenated.

[Synthesis of Monoene Compound]

As the diene compounds which can be used for synthesizing the monoene compound (hereinafter, merely "diene compound"), a hydrocarbon compound having a six-membered ring structure, having only a methyl group and an isopropyl group at 1-position and 4-position respectively of the six-membered ring and having two double bonds within a molecule can be used preferably.

Examples of the diene compounds include alicyclic hydrocarbons and terpene hydrocarbons. Preferable examples thereof include limonene, α-terpinene, β-terpinene, γ-terpinene, isolimonene, α-phellandrene, β-phellandrene, Menogenes, terpinolene and dipentene. More preferable examples thereof include limonene, α-terpinene, γ-terpinene, α-phellandrene, terpinolene and dipentene. Most preferable examples thereof include limonene in terms of availability.

Limonene is contained in large quantity in natural essential oils obtained from peels of oranges, lemon and grapefruits, and is easily produced in 98% purity by steam distillation. In addition, limonene is available at low cost since it is industrially produced for various other uses.

Hydrogenation catalysts for the diene compound are not particularly limited as long as it is commonly used for hydrogenation of unsaturated bonds. It is preferable to use a catalyst containing at least one selected from the metals belonging to 8-11 groups of the periodic table.

More specifically, it is preferable to use a catalyst containing at least one selected from the group consisting of iron, cobalt, nickel, copper, ruthenium, rhodium, palladium, silver, osmium, iridium, platinum and gold.

The hydrogenation catalyst can be a solid catalyst or a homogeneous catalyst. It is preferable to use a solid catalyst in terms of separativity from the reactant.

Examples of the solid catalysts include a non-carrying type metal catalyst and a carried metal catalyst. Preferable examples of the non-carrying type metal catalysts include (1) a Raney catalyst such as Raney nickel, Raney cobalt and Raney copper and (2) oxides of platinum, palladium, rhodium and ruthenium and a colloidal catalyst thereof.

Examples of the carried metal catalysts include a catalyst wherein at least one metal selected from the group consisting of iron, cobalt, nickel, copper, ruthenium, rhodium, palladium, silver, osmium, iridium, platinum and gold is(are) carried on or mixed with a carrier such as magnesia, zirconia, ceria, diatom earth, activated carbon, alumina, silica, zeolite and titania.

Preferable examples thereof include a carried copper catalyst wherein a copper catalyst is carried on a carrier such as a Cu—Cr catalyst (Adkins Catalyst), a Cu—Zn catalyst and a Cu—Fe catalyst, a carried platinum catalyst such as a Pt/C catalyst and a Pt/alumina catalyst, a carried palladium catalyst such as a Pd/C catalyst and a Pd/alumina catalyst, a carried ruthenium catalyst such as a Ru/C catalyst and a Ru/alumina catalyst and a carried rhodium catalyst such as a Rh/C catalyst and a Rh/alumina catalyst. Among them, it is preferable to use a catalyst containing copper in terms of reactivity and selectivity.

When a copper catalyst is used, reactivity and selectivity thereof can be improved by activating the catalyst in a solvent such as heptane at 140-200° C. under hydrogen pressure of 1-3 MPa, before subjecting to the reaction of diene compounds.

The used amount of the hydrogenation catalyst depends on the type of catalyst. It is appropriate to use the catalyst in an amount of 0.001-100% by mass, preferably 0.01-30% by mass, more preferably 0.1-20% by mass based upon the amount of the diene compound which is a raw material.

The pressure of hydrogen can be a normal pressure or an applied pressure. The pressure is usually in the range of 0.1-4.0 MPa, preferably 0.1-3.0 MPa, more preferably 0.1-2.0 MPa.

Hydrogenation reaction can be carried out in a solvent-free condition or by using a solvent. Examples of the solvents include water, organic acids such as formic acid and acetic acid; aromatic compounds such as benzene, o-dichlorobenzene, toluene and xylene; hydrocarbons such as hexane, heptane and cyclohexane; alcohols such as methanol, ethanol, isopropyl alcohol, t-butyl alcohol, ethylene glycol and diethylene glycol; ethers such as dioxane, tetrahydrofuran, dimethoxyethane and diglyme; and mixtures thereof.

The amount of solvents to be used for hydrogenation reaction is usually in the range of 0.1-30 times by mass, preferably 0.2-20 times by mass based upon the amount of the diene compound which is a raw material.

The reaction temperature of the hydrogenation reaction is usually from −90° C. to 200° C., preferably from 20° C. to 150° C., more preferably 20° C. to 100° C.

The form of hydrogenation reaction is not particularly limited as long as catalytic hydrogenation reaction can be carried out. Known methods normally employed can be employed. Examples thereof include a suspended-bed reactor wherein catalytic hydrogenation reaction is carried out by fluidizing a catalyst in fluid and a solid-bed reactor wherein catalytic hydrogenation reaction is carried out by feeding fluid whereas a catalyst is filled and fixed.

[Carbon Monoxide]

Carbon monoxide to be used for the carbonylation process of the present invention can contain inert gasses such as nitrogen and methane. The carbonylation reaction is carried out preferably under a partial pressure of carbon monoxide of 0.5-5 MPa, more preferably 1-3 MPa. When the partial pressure of carbon monoxide is 0.5 MPa or higher, the carbonylation reaction can progress sufficiently to obtain an alicyclic carbonyl compound which is a target compound in a high yield, without accompanying side reactions such as disproportionation reaction and polymerization. The partial pressure of carbon monoxide is preferably 5 MPa or lower in terms of an equipment load.

[Hydrogen Fluoride]

HF to be used for the carbonylation process is used in substantially anhydrous state, since it is used as a reaction solvent, as a catalyst and as an auxiliary material of the process. HF is used usually in an amount of 4-15 mol times, preferably 6-10 mol times to the amount of the monoene compound which is a raw material. When the molar ratio of HF is 4 mol times or more, the carbonylation reaction can progress efficiently, side reactions such as disproportionation reaction and polymerization can be inhibited and an alicyclic carbonyl compound which is a target compound can be obtained in a high yield. The used amount of HF is preferably 15 mol times or less in terms of cost of low materials and productivity.

[Reaction Conditions]

The form of the carbonylation reaction is not particularly limited and any methods such as batch reaction, semicontinuous reaction and continuous reaction can be employed.

The reaction temperature of the carbonylation reaction is preferably from −50° C. to 30° C., more preferably from −40° C. to 0° C., most preferably −30° C. to −25° C. When the reaction temperature of the carbonylation reaction is 30° C. or lower or particularly −25° C. or lower, high selectivity would be achieved. It is preferable to carry out the reaction at a temperature of −50° C. or higher in terms of reaction rate.

<(b) Isomerization Process>

Regarding the isomerization of acid fluoride represented by chemical formula (3) to acid fluoride represented by chemical formula (4), the isomerization reaction can be carried out, after once separating the acid fluoride, again in the presence of HF catalyst, or usually, the reaction mixture obtained by the carbonylation reaction can be subjected to the isomerization reaction directly without separating the acid fluoride.

The isomerization reaction is carried out under from normal pressure to very little pressure of carbon monoxide. The carbon monoxide partial pressure at this time is preferably 0.1-2 MPa, more preferably 0.1-1 MPa. When the carbon monoxide partial pressure is higher than 2 MPa, isomerization reaction might not progress sufficiently. The lower the carbon monoxide partial pressure is, the better in terms of yield. When the carbon monoxide partial pressure is lower than 0.1 MPa, modification of acid fluoride might occur. Therefore, the carbon monoxide partial pressure is preferably 0.1 MPa or higher.

The reaction temperature of the isomerization process is preferably in the range from 0° C. to 50° C., more preferably in the range from 10° C. to 30° C., in light of reaction rate, suppression of degradation of acid fluoride, and suppression of isomerizing to other isomers.

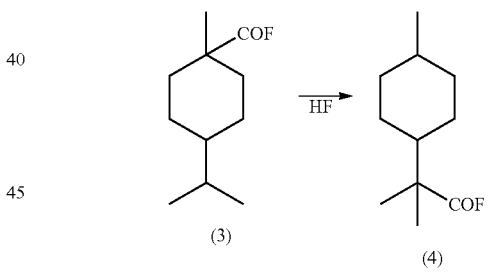

<(c) Esterification Process>

The reaction mixture of acid fluoride produced by the isomerization reaction is then reacted with alcohol having 1-4 carbon atoms to produce an alicyclic ester compound. At this time, it is preferable to employ a method wherein a predetermined amount of alcohol is added into the reaction mixture of acid fluoride, in terms of corrosivity of reaction apparatus.

The reaction mixture of acid fluoride produced by the isomerization reaction (I) can be used as a raw material for the next process which is a carbonyl group-reduction process in the form of acid fluoride after distilling excess HF away and purifying by a conventional method such as distillation, or (II) can be subjected to hydrolysis to obtain a corresponding carboxylic acid compound after distilling excess HF away, and then said carboxylic acid compound can be used as a raw material for the next process which is a carbonyl group-reduction process after purifying by a conventional method such as distillation.

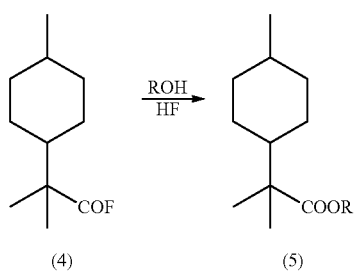

(4) → (5)

In the above chemical formula, R represents an alkyl group having 1-4 carbon atoms.

Examples of alcohols to be used for the above esterification process include methanol, ethanol, n-propanol, i-propanol, n-butyl alcohol, 1-butyl alcohol and t-butyl alcohol. Among them, it is preferable to use methanol or ethanol in terms of reactivity.

Alcohol can be used in an amount of preferably 0.5-2.0 mol times, more preferably 0.8-1.5 mol times to the amount of the monoene compound which is a raw material of the carbonylation process. The molar ratio of alcohol of 0.5 mol times or more is preferable because the remaining amount of the unreacted fluoride is small and corrosion of equipment in the following processes can be inhibited. The molar ratio of alcohol of 2.0 mol times or less is preferable because dehydration reaction among alcohol molecules can be suppressed and corrosion of equipment can be inhibited.

The reaction temperature of reaction between acid fluoride and alcohol is from −40° C. to 20° C. in terms of degradation inhibition of a cyclohexane carbonyl compound represented by the general formula (5). When the reaction temperature is lower than −40° C., esterification reaction rate might become low and the yield might be decreased. When the reaction temperature is higher than 20° C., the risk of producing water as a by-product in the reaction system might be increased because of causing degradation of ester, dehydration reaction of added alcohol or the like.

The cyclohexane carbonyl compound represented by the general formula (5) thus obtained is purified by conventional methods such as distillation after distilling HF away.

<(d) Carbonyl Group-Reduction Process>

Reduction of the cyclohexane carbonyl compound represented by the general formula (5) obtained in the above esterification process can be carried out by any conventional methods for reducing a carbonyl compound to an alcohol compound, which is not particularly limited. For example, any methods shown in the Fifth Series of Experimental Chemistry, Vol. 14 (Maruzen Publishing Co., Ltd.), pages 11-27, such as hydride reduction, reduction by metal and metal salts and catalytic hydrogenation can be employed. In terms of economic efficiency, reduction by catalytic hydrogenation is preferable.

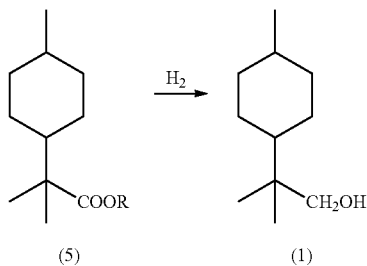

(5) → (1)

Catalysts to be used for catalytic hydrogenation of cyclohexane carbonyl compounds are not particularly limited as long as it is a normal catalyst used for hydrogenation if a carbonyl compound. It is preferable to use a catalyst containing at least one selected from the group consisting of metals belonging to 8-11 groups of the periodic table.

Particular examples thereof include a catalytic hydrogenation catalyst containing at least one selected from the group consisting of iron, cobalt, nickel, copper, ruthenium, rhodium, palladium, silver, osmium, iridium, platinum and gold.

The catalytic hydrogenation catalyst can be a solid catalyst or a homogeneous catalyst. It is preferable to use a solid catalyst in terms of separativity from the reactant.

Examples of the solid catalysts include a non-carrying type metal catalyst and a carried metal catalyst.

Preferable examples of the non-carrying type metal catalysts include (1) a Raney catalyst such as Raney nickel, Raney cobalt and Raney copper, and (2) oxides of platinum, palladium, rhodium and ruthenium and colloidal catalysts thereof.

Examples of the carried metal catalysts include a catalyst wherein at least one metal selected from the group consisting of iron, cobalt, nickel, copper, ruthenium, rhodium, palladium, silver, osmium, iridium, platinum and gold is(are) carried on or mixed with a carrier such as magnesia, zirconia, ceria, diatom earth, activated carbon, alumina, silica, zeolite and titania.

Preferable examples thereof include a carried copper catalyst wherein a copper catalyst is carried on a carrier such as a Cu—Cr catalyst (Adkins Catalyst), a Cu—Zn catalyst and a Cu—Fe catalyst, a carried platinum catalyst such as a Pt/C catalyst and a Pt/alumina catalyst, a carried palladium catalyst such as a Pd/C catalyst and a Pd/alumina catalyst, a carried ruthenium catalyst such as a Ru/C catalyst and a Ru/alumina catalyst and a carried rhodium catalyst such as a Rh/C catalyst and a Rh/alumina catalyst. Among them, it is preferable to use a catalyst containing at least one selected from the group consisting of nickel and copper in terms of reactivity.

The used amount of the catalytic hydrogenation catalyst depends on the type of catalyst. It is appropriate to use the catalyst in an amount of 1-100% by mass, preferably 3-30% by mass based upon the amount of the cyclohexane carbonyl compound which is a raw material.

[Solvent]

The carbonyl group-reduction process of the present invention can be carried out in a solvent-free condition or by using a solvent.

Examples of the solvents for the carbonyl group-reduction process of the present invention include water, organic acids such as formic acid and acetic acid; aromatic compounds such as benzene, o-dichlorobenzene, toluene and xylene; hydrocarbons such as hexane, heptane and cyclohexane; alcohols such as methanol, ethanol, isopropyl alcohol, t-butyl alcohol, ethylene glycol and diethylene glycol; ethers such as dioxane, tetrahydrofuran, dimethoxyethane and diglyme; and mixtures thereof.

Among them, it is preferable to carry out the process in a solvent-free condition or by using a solvent selected from aromatic compounds such as benzene, o-dichlorobenzene, toluene and xylene; hydrocarbons such as hexane, heptane and cyclohexane; alcohols such as methanol, ethanol, isopropyl alcohol, t-butyl alcohol, ethylene glycol and diethylene glycol; ethers such as dioxane, tetrahydrofuran, dimethoxyethane and diglyme; and mixtures thereof.

The amount of solvents in the case of using solvents for carbonyl group-reduction process of the present invention is usually in the range of 0-30 times by mass, preferably 0-20 times by mass based upon the amount of the cyclohexane carbonyl group represented by the general formula (5) obtained in the esterification process.

[Reaction Conditions]

As for the hydrogen pressure in the carbonyl group-reduction process of the present invention, it is preferable to carry out under high pressure in terms of shifting the reaction equilibrium to the alcohol side. In consideration of facility cost, the hydrogenation pressure is preferably 1-30 MPa, more preferably 2-20 MPa, most preferably 5-10 MPa.

The reaction temperature of the carbonyl group-reduction process of the present invention is preferably 100° C. or higher, more preferably 150° C. or higher, in terms of obtaining sufficient reaction rate.

The reaction temperature thereof is preferably 300° C. or lower, more preferably 280° C. or lower, most preferably 250° C. or lower, in terms of inhibiting transesterification reaction between an alicyclic alcohol to be produced and the cyclohexane carbonyl compound represented by the general formula (5).

The form of the carbonyl group-reduction process of the present invention is not particularly limited. Also in the case of carrying out by catalytic hydrogenation, it is not particularly limited as long as catalytic hydrogenation reaction can be carried out. Known methods normally employed can be employed.

Examples thereof include a suspended-bed reactor wherein catalytic hydrogenation reaction is carried out by fluidizing a catalyst in fluid and a solid-bed reactor wherein catalytic hydrogenation reaction is carried out by feeding fluid whereas a catalyst is filled and fixed.

During the reaction, alcohols having 1-4 carbon atoms are produced as by-products. The reaction can be carried out in the presence of these by-product alcohols or can be carried out by removing them continuously or intermittently during the reaction.

After removing hydrogenation catalyst from the alicyclic alcohol compound thus obtained, purification is carried out by common methods such as distillation, whereby a novel alicyclic alcohol compound represented by the formula (1) can be obtained in high purity.

EXAMPLES

The present invention will be described in more detail below, referring to Examples and Comparative Examples, which are not intended to limit the scope of the present invention.

In the Examples and Comparative Examples described below, if not otherwise specified, "%" represents "% by mass".

<Gas Chromatography Analysis>

Analyses of a monoene compound and an alicyclic alcohol compound were carried out by gas chromatography using "GC-17A", trade name, manufactured by Shimadzu Corporation, and "HR-1", trade name, manufactured by Shinwa Chemical Industries Ltd.; 0.32 mmΦ×25 m, as a capillary column. The temperature was raised from 100° C. to 250° C. at the rate of 2° C./min.

Analysis of a cyclohexane carbonyl compound was carried out by gas chromatography using "GC-17A", trade name, manufactured by Shimadzu Corporation, and "DBWAX", trade name, manufactured by J & W; 0.32 mmΦ×30 m×0.25 µm, as a capillary column. The temperature was raised from 100° C. to 250° C. at the rate of 5° C./min.

Preparation Example 1

Preparation of 4-isopropyl-1-methyl cyclohexene (Hereinafter, "DH-Terpinene" by Hydrogenation of Limonene

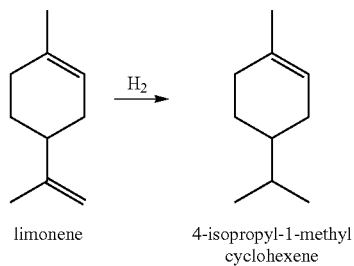

limonene      4-isopropyl-1-methyl cyclohexene 50.0 g of Cu—Cr catalyst, trade name "N-203S", manufactured by JGC Catalysts and Chemicals Ltd., and 500.0 g of heptane, a special grade reagent manufactured by Wako Pure Chemical Industries, Ltd., were charged into a 5L stainless-steel autoclave equipped with a NAC drive-type stirrer, three inlet nozzles at the top and an outlet nozzle at the bottom which has ability to regulate internal temperature by a jacket. Activation was carried out for 1 hour at 170° C. under hydrogen pressure of 2 MPa.

After cooling, 500.0 g of limonene, manufactured by YASUHARA CHEMICAL CO., LTD., was charged therein and hydrogenation reaction was carried out by stirring for 3 hours at 95° C. under hydrogen pressure of 2 MPa.

The reaction mixture thus obtained was then filtered to remove catalyst to obtain 957.4 g of a reaction mixture having the 4-isopropyl-1-methylcyclohexene concentration of 49.0%, the 4-isopropyl-1-methylcyclohexane concentration of 1.4% and the heptane concentration of 49.6%, wherein the yield was 92.5%.

Example 1

Carbonylation, Isomerization and Esterification of DH-Terpinene to Produce ethyl 2-methyl-2-(4-methylcyclohexyl)propionate (Hereinafter, "DHT-Ester"

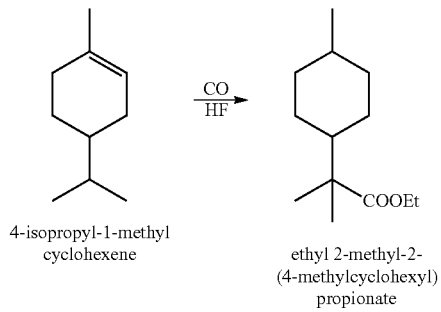

4-isopropyl-1-methyl cyclohexene      ethyl 2-methyl-2-(4-methylcyclohexyl) propionate <Carbonylation Process>

The experiment was carried out by using a 500 mL stainless-steel autoclave equipped with a NAC drive-type stirrer, three inlet nozzles at the top and one outlet nozzle at the bottom which has ability to regulate internal temperature by a jacket.

Firstly, the atmosphere in the autoclave was replaced with carbon monoxide, and then, 105 g (5.3 mol) of hydrogen fluoride was introduced therein. After regulating the liquid temperature at −30° C., the pressure was increased to 2 MPa by carbon monoxide.

Keeping the reaction temperature at −30° C. and the reaction pressure at 2 MPa, 211.3 g of the reaction mixture prepared in the Preparation Example 1 having the 4-isopropyl-1-methylcyclohexene concentration of 49.0%, the 4-isopropyl-1-methylcyclohexane concentration of 1.4% and the heptane concentration of 49.6% containing 0.75 mol of 4-isopropyl-1-methylcyclohexene was fed into the autoclave through the top, and the carbonylation reaction was carried out. After completion of feeding, stirring was continued for approximately 10 minutes until the absorption of carbon monoxide became unobserved.

A sample of the reaction mixture thus obtained was taken into cooled ethanol and water was added to separate into an oil phase and water phase. The oil phase was neutralized and was washed with water. The oil phase thus obtained was analyzed by gas chromatography, and as a result, it was found that a mixture having the isomer ratio of 93.5% of ethyl 4-isopropyl-1-methylcyclohexane carboxylate as the total of a cis isomer and a trans isomer, the isomer ratio of 2.2% of ethyl 2-methyl-2-(4-methylcyclohexyl)propionate and 4.2% of other isomers was obtained.

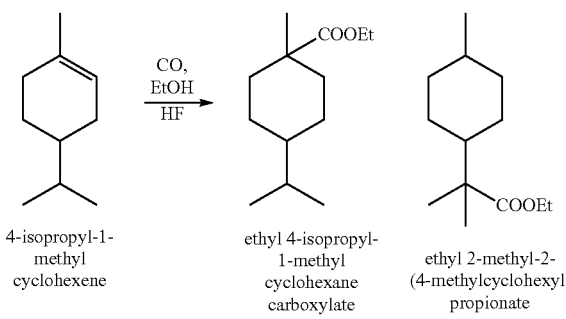

4-isopropyl-1-methyl cyclohexene ethyl 4-isopropyl-1-methyl cyclohexane carboxylate ethyl 2-methyl-2-(4-methylcyclohexyl) propionate <Isomerization Process and Esterification Process>

Subsequently, keeping the pressure of carbon monoxide at 1 MPa, the reaction temperature was raised to 25° C. and the temperature was kept at 25° C. for 24 hours. After 24 hours and descending the reaction temperature to 0° C., 51.8 g (1.12 mol) of ethanol was fed into the autoclave through the top and the esterification reaction was carried out for 1 hour under stirring.

The reaction mixture was extracted from the bottom of the autoclave into ice water, and was separated into an oil phase and a water phase. The oil phase was washed twice with 100 ml of 2% sodium hydroxide solution and twice with 100 ml of distilled water, and was dehydrated with 10 g of anhydrous sodium sulfate.

The liquid thus obtained was analyzed by gas chromatography, and as a result, it was found that a mixture having the isomer ratio of 52.4% of ethyl 4-isopropyl-1-methylcyclohexane carboxylate as the total of a cis isomer and a trans isomer, the isomer ratio of 40.3% of ethyl 2-methyl-2-(4-methylcyclohexyl)propionate and 7.2% of other isomers was obtained.

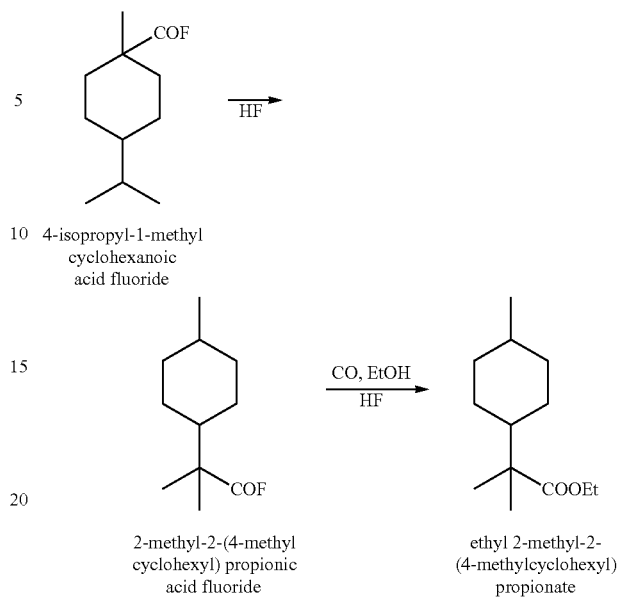

4-isopropyl-1-methyl cyclohexanoic acid fluoride 2-methyl-2-(4-methyl cyclohexyl) propionic acid fluoride ethyl 2-methyl-2-(4-methylcyclohexyl) propionate After removing low boiling components by an evaporator from the liquid thus obtained, rectification was carried out by a rectifier having the theoretical stage number of 20 at the distillation temperature of 150° C. under vacuum degree of 60 torr, whereby 136.1 g of a mixture of esters having the isomer ratio of 52.1% of ethyl 4-isopropyl-1-methylcyclohexane carboxylate as the total of a cis isomer and a trans isomer, the isomer ratio of 40.8% of ethyl 2-methyl-2-(4-methylcyclohexyl) propionate and 7.1% of other isomers was obtained as a main fraction of distillate, wherein the yield of ethyl 2-methyl-2-(4-methylcyclohexyl) propionate was 34.9 mol % based on 4-isopropyl-1-methylcyclohexene.

Carbonyl Group-Reduction Process; Production of DHT-Alcohol {2-methyl-2-(4-methylcyclohexyl) propan-1-ol} by Reducing DHT-Ester

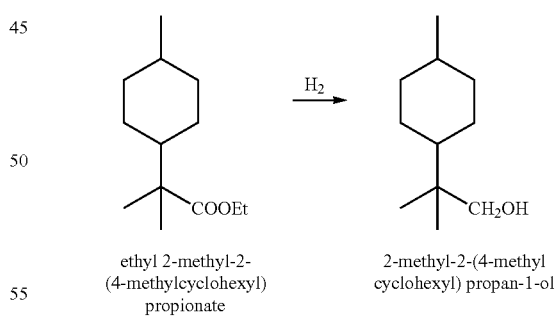

ethyl 2-methyl-2-(4-methylcyclohexyl) propionate 2-methyl-2-(4-methyl cyclohexyl) propan-1-ol 5.3 g of Cu—Zn catalyst carried on alumina, manufactured by JGC Catalysts and Chemicals Ltd., 105 g of the mixture of esters obtained in the above-mentioned main fraction of distillate containing 52.1% of ethyl 4-isopropyl-1-methylcyclohexane carboxylate, 40.8% of ethyl 2-methyl-2-(4-methylcyclohexyl) propionate and 7.1% of other isomers were charged into a stainless-steel autoclave and reduction reaction was carried out by stirring for 14 hours at 260° C. under 10 MPa of hydrogen pressure while flowing hydrogen gas without the use of solvents.

After filtrating the reaction mixture to remove catalyst, 68 g of a product which was a mixture containing 41.0% of (cis-4-isopropyl-1-methylcyclohexyl)methanol and 39.0% of 2-methyl-2-(4-methylcyclohexyl) propan-1-ol was produced, wherein the yield of 2-methyl-2-(4-methylcyclohexyl) propan-1-ol was 77.2 mol % based on ethyl 2-methyl-2-(4-methylcyclohexyl) propionate.

After removing low boiling components by an evaporator from the mixture thus obtained, rectification was carried out by a rectifier having the theoretical stage number of 20 to isolate the main product. The fraction of distillate thus obtained had 84.3% of purity and had excellent floral-green-like fragrance with a crisp and fresh feeling.

As a result of GC-MS analysis, the molecular weight thereof was found to be 170 which was same as the molecular weight of the intended compound.

As a result of 1H-NMR spectrum measured in a heavy chloroform solvent, the chemical shifts (δppm, TMS standard) were found at 3.38 (s, 2H), 1.69-1.75 (m, 2H), 1.67-1.71 (m, 2H), 1.38 (br, 1H), 1.21-1.30 (m, 1H), 1.15-1.23 (m, 1H), 0.98-1.08 (m, 2H), 0.85-0.94 (m, 2H), 0.86 (d, J=6.4 Hz, 3H), and 0.83 (s, 6H), whereby it was identified as 2-methyl-2-(4-methylcyclohexyl) propan-1-ol represented by formula (1).

Example 2

Floral-Type Perfume Composition 10 parts by mass of the alicyclic alcohol compound represented by chemical formula (1) which was obtained in Example 1 was mixed with 90 parts by mass of a perfume composition having a composition shown in Table 1, whereby a floral-type perfume composition characterized in crisp flavor evoking muguet.

TABLE 1

| perfumes | Parts by mass |
| --- | --- |
| phenyl hexanol | 30 |
| phenyl ethyl alcohol | 20 |
| methyl dihydrojasmonate | 10 |
| ethyl linalool | 8 |
| geranium oil | 6 |
| o-tert-butyl cyclohexyl acetate | 5 |
| acetylcedrene | 5 |
| cyclopentadecanolide | 5 |
| cis-3-hexenol | 0.8 |
| indole | 0.2 |
| Total | 90 |

Comparative Example 1

10 parts by mass of terpineol was mixed with 90 parts by mass of the perfume composition having a composition shown in Table 1. The resulting composition had a flavor lacking of briskness having an impression of camphor.

Comparative Example 2

10 parts by mass of cyclomethylene citronellol, trade name, manufactured by Firmenich, was mixed with 90 parts by mass of the perfume composition having a composition shown in Table 1. The resulting composition had a flavor wherein a rose perfume was enhanced.

Since the alicyclic alcohol compound obtained in Example 1 had a crisp green feeling as well, it can enhance a muguet fragrance more.

INDUSTRIAL APPLICABILITY

The novel alicyclic alcohol compound of the present invention is novel in terms of having excellent floral-green-like fragrance with a crisp and fresh feeling. Because of its excellent fragrance sustaining properties, it is useful as a perfuming ingredient for a wide variety of products such as toiletry products, soaps and detergent for clothing.

In addition, the manufacturing method for producing the alicyclic alcohol compound of the present invention enables to produce said alicyclic alcohol compound by an industrially beneficial process.

The invention claimed is:
1. An alicyclic alcohol compound of formula (1)

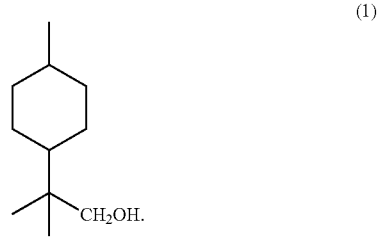

2. A perfume composition, comprising the alicyclic alcohol compound of claim 1

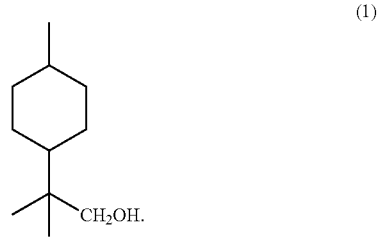

3. A method for manufacturing the alicyclic alcohol compound of claim 1, comprising
  reacting, in the presence of hydrogen fluoride, 4-isopropyl-1-methylcyclohexene of formula (2) with carbon monoxide to obtain 4-isopropyl-1-methylcyclohexane carboxylic acid fluoride of formula (3),
  isomerizing the 4-isopropyl-1-methylcyclohexane carboxylic acid fluoride of formula (3) to obtain 2-methyl-2-(4-methylcyclohexyl) propionyl fluoride of formula (4),
  reacting 2-methyl-2-(4-methylcyclohexyl) propionyl fluoride with alcohol to obtain a cyclohexane carbonyl compound of formula (5), and
  reducing the cyclohexane carbonyl compound of formula (5) to obtain the alicyclic alcohol compound represented by chemical formula (1),

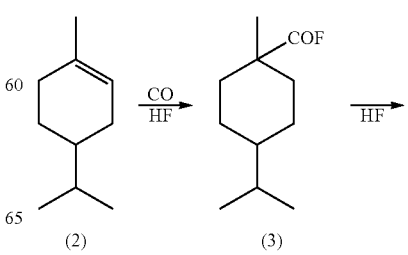

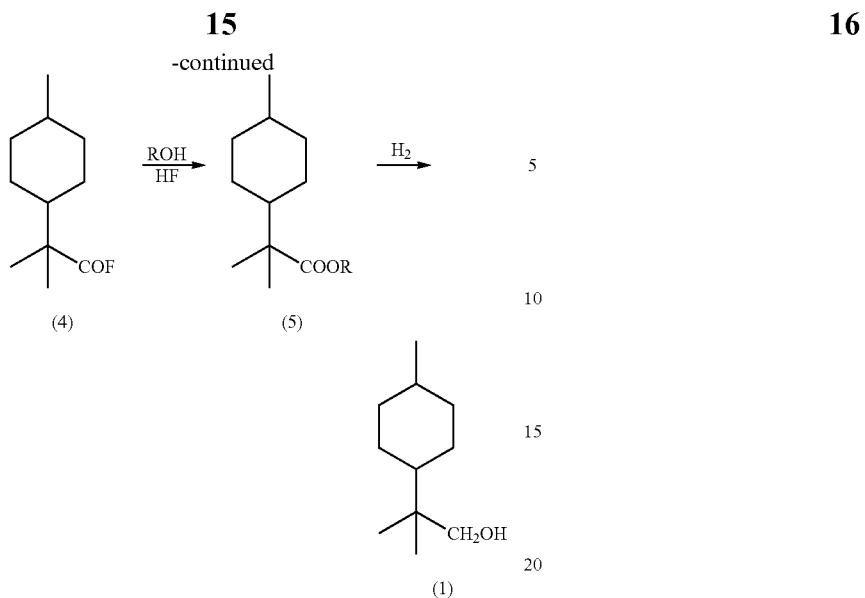
wherein "R" is an alkyl group having 1-4 carbon atoms.
* * * * *